(12) United States Patent
Tada et al.

(10) Patent No.: US 7,141,601 B2
(45) Date of Patent: Nov. 28, 2006

(54) DENDRITE ELONGATION INHIBITOR FOR MELANOCYTE AND SKIN PREPARATION FOR EXTERNAL USE CONTAINING THE SAME

(75) Inventors: Akihiro Tada, Yokohama (JP); Akiko Kanamaru, Yokohama (JP); Yuko Saeki, Yokohama (JP)

(73) Assignee: Pola Chemiocal Industries Inc., Shizuoka (JP)

( * ) Notice: Subject to any disclaimer, the term of this patent is extended or adjusted under 35 U.S.C. 154(b) by 0 days.

(21) Appl. No.: 10/536,675

(22) PCT Filed: Nov. 28, 2003

(86) PCT No.: PCT/JP03/15266

§ 371 (c)(1),
(2), (4) Date: May 27, 2005

(87) PCT Pub. No.: WO2004/050053

PCT Pub. Date: Jun. 17, 2004

(65) Prior Publication Data

US 2005/0288361 A1    Dec. 29, 2005

(30) Foreign Application Priority Data

Dec. 2, 2002    (JP) ............... 2002-349376

(51) Int. Cl.
*A01N 43/16* (2006.01)
*A61K 31/35* (2006.01)
*C07D 311/04* (2006.01)
*C07D 311/74* (2006.01)
*C07D 311/76* (2006.01)

(52) U.S. Cl. ................... 514/456; 549/402
(58) Field of Classification Search ........... 549/402; 514/456

See application file for complete search history.

(56) References Cited

U.S. PATENT DOCUMENTS

2002/0065300 A1    5/2002    Seiberg et al.

FOREIGN PATENT DOCUMENTS

| JP | 08-133949 | 5/1996 |
| JP | 08-208451 | 8/1996 |
| JP | 10-287544 | 10/1998 |
| JP | 11-079968 | 3/1999 |
| JP | 2000-13718 | 4/2000 |
| JP | 2000-103718 | 4/2000 |
| JP | 2001335485 | * 12/2001 |
| WO | 01/56580 | * 9/2001 |

OTHER PUBLICATIONS

Zhu et al., "Separation and determination of homoisoflavonoids in Ophiopogon japonicus by reversed-phase high-performance liquid chromatography", Journal of Chromatography, vol. 437, pp. 265-267.*

Kaneda et al., "Studies on the components of ophiopogon roots (China). I", Yakugaku Zasshi, vol. 103, pp. 1133-1139.*

Tada et al., Studies on the constituents of ophiopogonis tuber. V. Isolation of a novel class of homoisoflavonoids and determination of their structures (1), Chemical & pharmaceuticla Bulletin, vol. 28, pp. 1477-1484.*

Huang et al., "Benzoquinones, a homoisoflavanone and other constituents from polygonatum alte-lobatum", Phytochemistry, vol. 44, pp. 1369-1373.*

Yoshiaki et al., "Comparative studies on the constituents of ophiopogonis tuber and its congeners. IV. studies on the homoisoflavonoids of the subterranean part of ophiopogon ohwii Okuyama and O.jaburan (Kunth) Lodd", Chemical & Pharmaceutical Buletin, vol. 33, pp. 5358-5363.*

Takatsuki et al., "Cytotoxic components of ophiopogonis tuber", Natural Medicines, vol. 52, pp. 145-150.*

Watanabe et al., "Comparative studies on the constituents of ophiopogonis tuber and its congeners (part V), studies on the constituents of the subterranean part of ophiopogon chekiangensis Kimura et H. Migo.", Shoyakugaku Zasshi, vol. 44, pp. 117-121.*

Zhu et al., "Isolation and identification of homoisoflavanor from Maidong", Yaoxue Xue bao, vol. 22, pp. 679-684.*

Watanabe, et al. "Comparative Studies on the Constituents of Ophiopogonis Tuber and Its Congeners IV. Studies on the Homoisoflavonoids of the Subterranean Part of *Ophiopogon ohwii* Ikuyama and *O. jaburan* (Kunth) Lodd," *Chem. Pharm. Bull.*, vol. 33, No. 12, pp. 5358-5363, 1985.

International Search Report issued to a related foreign application.

* cited by examiner

*Primary Examiner*—Thomas Mckenzie
*Assistant Examiner*—Niloofar Rahmani
(74) *Attorney, Agent, or Firm*—Knobbe, Martens, Olson & Bear, LLP

(57) ABSTRACT

The present invention relates to a dendrite elongation inhibitor for melanocytes consisting of a compound represented by the following general formula (1):

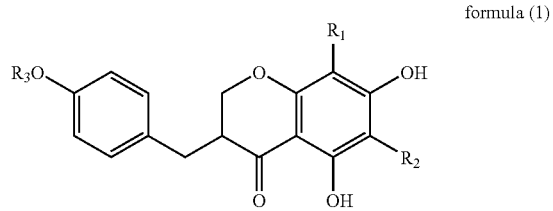

formula (1)

and/or a salt thereof,
wherein $R_1$, $R_2$, and $R_3$ each independently represent a $C_{1-4}$ alkyl group or hydrogen atom,
and a skin preparation for external use comprising the dendrite elongation inhibitor for melanocytes as an active ingredient.

4 Claims, No Drawings

DENDRITE ELONGATION INHIBITOR FOR MELANOCYTE AND SKIN PREPARATION FOR EXTERNAL USE CONTAINING THE SAME

RELATED APPLICATIONS

This application is the U.S. National Phase under 35 U.S.C. § 371 of International Application PCT/JP2003/015266, filed Nov. 28, 2003, which was published in a language other than English, which claims priority of JP 2002-349376, filed Dec. 2, 2002.

TECHNICAL FIELD

The present invention relates to a dendrite elongation inhibitor for melanocytes and a skin preparation for external use containing the dendrite elongation inhibitor for melanocytes as an active ingredient.

BACKGROUND ART

Keeping skins fair and beautiful is what many women hope, and many whitening cosmetics have therefore been developed. For example, whitening cosmetics can be exemplified by cosmetics containing ascorbic acid or a derivative thereof, kojic acid or a derivative thereof, tranexamic acid or a derivative thereof, hydroquinone glycoside, or the like. However, most of the cosmetics have a mechanism utilizing the action of inhibiting tyrosinase and inhibiting the biosynthesis of melanin, and we had to say that there is a limit on its effect. That is, even though the whitening cosmetics containing those ingredients as active ingredients are effective for symptoms such as age spots, freckles, and dark complexion that result from the abnormally accelerated production of melanin, we had to say that such whitening cosmetics do not have much effect on dyschromatosis to which the amount of melanin produced less contributes. In other words, there exists dyschromatosis for which tyrosinase inhibitors are not or less effective, and it has been desired that means for alleviating such dyschromatosis is developed.

On the other hand, examples of dyschromatosis to which the amount of melanin produced less contributes include those resulting from the accelerated migration of melanin granules from melanocytic dendrites. Although it is considered for such dyschromatosis to treat by inhibiting the elongation of dendrites that occurs when melanocytes allows melanin granules to migrate, not so many whitening agents utilizing such a mechanism have been known. That is, it can be said that there has been a demand for the development of whitening agents utilizing such a mechanism.

On the other hand, Ophiopogon Tuber (Bakumondo) has widely been used in Chinese herbal medicines for the purpose of improving body fluids (JP-A 2000-103718). Although it has been also already known that Ophiopogon Tuber is incorporated as an active ingredient having moisture retention (JP-A 11-79968), as a melanin production inhibitor (JP-A 08-133949), and as a lipid-degrading agent (JP-A 2000-103718) in the field of skin preparations for external use such as cosmetics, a compound represented by the following general formula (1) and/or a salt thereof, which is an ingredient incorporated in the Ophiopogon Tuber such as methylophiopogonanone B (2,3-dihydro-3-[(4-methoxyphenyl)methyl]-5,7-dihydroxy-6,8-dimethyl-4H-1-benzopyran-4-on; hereinafter, also referred to as "Compound 1") have (has) not been known in the least to inhibit the elongation of melanocytic dendrites, nor known to be useful for alleviating, by this action, dyschromatosis on which melanin production inhibitors utilizing usual tyrosinase inhibitory action are not or less effective.

Moreover, a compound represented by the general formula (1) and/or a salt thereof such as methylophiopogonanone B have (has) been known to be incorporated in Ophiopogon Tuber or the like (Watanabe Yoshiaki el. al., Chemical & Pharmaceutical Bulltin, (1985), 33(12), 5358–5363), and separation methods thereof have also already been known.

DISCLOSURE OF THE INVENTION

The present invention has been achieved under such circumstances, and an object of the present invention is to provide a useful ingredient for inhibiting the elongation of melanocytic dendrites and alleviating, by this action, dyschromatosis on which melanin production inhibitors utilizing usual tyrosinase inhibitory action are not or less effective.

In light of such circumstances, the inventors of the present invention have conducted extensive studies and redoubled efforts to acquire a useful ingredient for inhibiting the elongation of melanocytic dendrites and alleviating, by this action, dyschromatosis on which melanin production inhibitors utilizing usual tyrosinase inhibitory action are not or less effective. As a result, the inventors of the present invention have completed the present invention by finding out that a compound represented by the general formula (1) and/or a salt thereof, which is incorporated in Ophiopogon Tuber have (has) such action. Namely, the present invention relates to a technique shown below.

(1) A dendrite elongation inhibitor for melanocytes consisting of a compound represented by the following general formula (1):

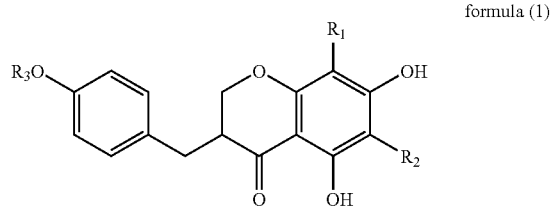

and/or a salt thereof, wherein $R_1$, $R_2$, and $R_3$ each independently represent a $C_{1-4}$ alkyl group or hydrogen atom.

(2) The dendrite elongation inhibitor for melanocytes according to (1), characterized in that the compound represented by the general formula (1) is methylophiopogonanone B indicated by the following formula.

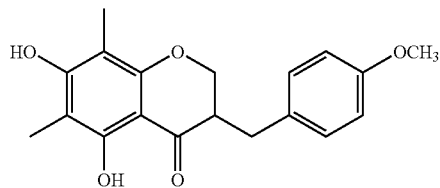

(3) A skin preparation for external use for inhibiting elongation of melanocytic dendrites, comprising the dendrite elongation inhibitor for melanocytes according to (1) or (2) as an active ingredient.

(4) The skin preparation for external use for inhibiting elongation of melanocytic dendrites according to (3), characterized in that the skin preparation for external use is used for alleviating dyschromatosis on which tyrosinase inhibitors have insufficient effect.

(5) The skin preparation for external use for inhibiting elongation of melanocytic dendrites according to (3) or (4), characterized in that the skin preparation for external use is a cosmetic.

BEST MODE FOR CARRYING OUT THE INVENTION (1) Dendrite Elongation Inhibitor for Melanocyte of the Present Invention A dendrite elongation inhibitor for melanocytes of the present invention consists of a compound represented by the above-described general formula (1) and/or a salt thereof.

In the general formula (1), $R_1$, $R_2$, and $R_3$ each independently represent an alkyl group or hydrogen atom.

The alkyl group is preferably a $C_{1-4}$ alkyl group, and examples thereof include a methyl group, an ethyl group, a propyl group, a 1-methylethyl group, a n-butyl group, a 1-methylpropyl group, a 2-methylpropyl group, and a 1,1-dimethylethyl group. Of those, particularly preferred is a methyl group.

The compound represented by the general formula (1) can preferably be exemplified by methylophiopogonanone B (Compound 1).

Such a compound represented by the general formula (1) can be directly used, or can be used in a salt form after treatment with alkali.

The salt can be applied without particular limitation as long as it is physiologically acceptable, and can preferably be exemplified by alkali metal salts such as sodium salts and potassium salts, alkaline-earth metal salts such as calcium salts and magnesium salts, ammonium salts, organic amine salts such as triethanolamine salts, and triethylamine salts, and basic amino acid salts such as lysine salts and arginine salts. Particularly preferred are alkali metal salts, which are easy to be prepared.

In a skin preparation for external use of the present invention, the compound represented by the general formula (1) and/or the salt thereof can be incorporated alone or a combination of two or more kinds of them can be incorporated.

Such a compound represented by the general formula (1) and/or a salt thereof may be purified one, and may be an extract from a plant or a fraction thereof, or the like containing an effective amount of the compound represented by the general formula (1) and/or the salt thereof.

Plants of the genus *Ophiopogon* of the family Liliaceae, preferably *Ophiopogon japonicus* ker-Gawler can be used as such plants. A plant used in the extraction of the compound represented by the general formula (1) and/or the salt thereof maybe the entire plant, apart of the plant containing the compound represented by the general formula (1) and/or the salt thereof, or a processed product of the plant. For example, an extract of *Ophiopogon* tuber that is the aggregated root of a plant of the genus *Ophiopogon* of the family Liliaceae can be purified and fractionated to obtain the compound represented by the general formula (1) and/or the salt thereof. The compound represented by the general formula (1) and/or the salt thereof can be identified by X-ray analysis or the like.

The extract can particularly preferably be exemplified by an extract with a highly polar solvent. The highly polar solvent can preferably be exemplified by: ethers such as diethyl ether, isopropyl ether, and tetrahydrofuran; halogenated hydrocarbons such as methylene chloride and chloroform; esters such as ethyl-acetate and methyl formate; ketones such as acetone and methylethylketone; nitriles such as acetonitrile; alcohols such as 1,3-butanediol, ethanol, and isopropyl alcohol; and water. Of those, alcohols are particularly preferred. It is noted that the above-described solvent may be one kind or a mixture of two or more kinds of them.

Extraction may typically be carried out by adding 1 to 10 times by weight of a solvent with respect to the entire plant or a part of the plant, followed by a few-day immersion if carried out at room temperature or a few-hour immersion if carried out around a boiling point. After extraction, the solvent can be removed by vacuum concentration or the like, if necessary. The compound represented by the general formula (1) can be isolated from the extract from which solvent has been removed, by liquid-liquid extraction with ethyl acetate and water, and the like, or purification by silica gel column chromatography using, for example, chloroform-methanol as an eluting solvent, or the like.

A preferable content of the compound represented by the general formula (1) and/or the salt thereof in a skin preparation for external use of the present invention is 0.001 to 10% by weight, more preferably 0.005 to 5% by weight with respect to the total amount of the skin preparation for external use. This is because, if the content is too small, inhibitory action on the elongation of melanocytic dendrites may not be exhibited; while, if the content is too large, the action may level off and may unnecessarily inhibit the degree of freedom of a prescription.

(Example of Production)

Three kilograms of *Ophiopogon* tuber (aggregated root of *Ophiopogon japonicus* ker-Gawler of the genus *Ophiopogon* of the family Liliaceae) was cut into narrow pieces, which were then added to ethanol 101 and heated to reflux for 3 hours. After cooled to room temperature, the resulting mixture was concentrated under vacuum concentration, and 11 of ethyl acetate and water were added thereto. The resulting mixture was subjected to liquid-liquid extraction to take out the phase of ethyl acetate, followed by vacuum concentration. After dissolved in chloroform, the residue was charged on silica gel column chromatography and purified with an eluting solvent chloroform:methanol=100:1 to 70:30 to give 225 mg of Compound 1. The structure was determined by X-ray analysis.

(2) Skin Preparation for External Use of the Present Invention

A skin preparation for external use of the present invention is characterized by containing the above-described dendrite elongation inhibitor for melanocytes of the present invention. A skin preparation for external use used herein means a general term for compositions applied for external use for skins, and can be exemplified by cosmetics including quasi-drugs, dermatologic drugs for external use, and dermatologic sundry articles for external use. Of those, particularly preferred are cosmetics. This is because the above-described dendrite elongation inhibitor for melanocytes of the present invention has excellent safety, so that the dendrite elongation inhibitor for melanocytes can be used continually and habitually as cosmetics, and more satisfactorily exhibit whitening action in such a usage pattern.

The dosage forms of cosmetics are not particularly limited and the cosmetics can be used not only in emulsified dosage forms such as cream and milky lotions but in solution dosage forms such as skin lotions and essences, because the dendrite elongation inhibitor of the present invention has particularly high physical properties of polarity.

Skin preparation for external use of the present invention can contain the optional ingredients used generally in a skin preparation for external use, beside the dendrite elongation inhibitor for melanocytes described above. Preferable examples of the optional ingredients include: hydrocarbons such as squalene, liquid paraffin, light-gravity liquid isoparaffin, heavy-gravity liquid isoparaffin, microcrystalline wax, and solid paraffin; silicones such as dimethycon, femethycon, cyclomethycon, amodimethycon, polyether denatured silicone; esters such as jojoba oil, carnauba wax, haze wax, bees wax, spermaceti wax, octyldodecyl oleate, isopropyl myristate, neopentyl glycol diisostearate, and malic diisostearate; aliphatic acids such as stearic acid, lauric acid, myristic acid, palmitic acid, isostearic acid, isopalmitic acid, behenic acid, and oleic acid; higher alcohols such as behenyl alcohol (1-docosanol), cetanol, oleyl alcohol, and octadecyl alcohol; triglycerides such as castor oil, coconut oil, hydrofined coconut oil, camellia oil, wheat germ oil, isostearate triglyceride, isooctanoate triglyceride, and olive oil; polyhydric alcohols such as 1,3-butanediol, glycerin, diglycerin, dipropylene glycol, polyethylene glycol, 1,2-pentandiol, 1,2-hexylene glycol, and isoprene glycol; nonionic detergents such as sorbitan sesquiolate, sorbitan monooleate, sorbitan trioleate, sorbitan sesquistearate, sorbitan monostearate, polyoxyethylene sorbitan monooleate, polyoxyethylene sorbitan monostearate, polyoxyethylene stearate, polyoxyethyleneoleate, polyoxyethylene glyceril fatty ester, polyexyethylene alkyl ether, and polyoxyethylene hardened castor oil; anionic detergents such as sodium lauryl stearate, polyoxyethylene alkyl sulfate, and sulfosuccinate; cationic detergents such as quaternary alkyl ammonium salt; ampholytic detergents such as alkylbetaine; organicpowders such as crystalline cellulose, crosslinking type methylpolysiloxane, polyethylene powder, and acrylic resin powder; powders that can be surface-treated such as talc, mica, sericite, magnesium carbonate, calcium carbonate, titanium dioxide, iron oxide, iron blue, ultramarine, titanic mica, titanic sericite, and silica; thickening agents such as alkyl acrylate-alkyl methacrylate copolymer and/or a salt thereof, carboxyvinyl polymer and/or a salt thereof, xanthan gum, and hydroxypropyl cellulose; active ingredients such as vitamins, terpenes, and steroids; examples of vitamins include retinol, retinoic acid, tocopherol, riboflavin, pyridoxin, ascorbic acid, and ascorbic phosphate; examples of terpenes include glycyrrhizic acid salt, glycyrrhetin, ursolic acid, and oleanolic acid; examples of steroids include estradiol, ethynilestradiol, and estriol; antiseptic agents such as phenoxyethanol, parabens, Hibitane Gluconate, and benzalkonium chloride; and UV absorbing agents such as dimethylamino benzoate, cinnamates, and benzophenones.

Of course, a whitening agent having a different mechanism from that of the dendrite elongation inhibitor of the present invention, for example, ascorbic acid or a derivative thereof, kojic acid or a derivative thereof, tranexamic acid or a derivative thereof, hydroquinone glycoside, or the like, can also be incorporated in the skin preparation for external use. Incorporating such a whitening agent gives at least a synergistic effect and is therefore preferred. A preferable content of such a whitening agent having a different mechanism from that of the dendrite elongation inhibitor of the present invention is 0.01 to 5% by weight in total with respect to the total amount of the skin preparation for external use.

Applicable disease of the skin preparation for external use of the present invention can also preferably be exemplified by dyschromatosis on which tyrosinase inhibitors have insufficient effects. "Dyschromatosis on which tyrosinase inhibitors have insufficient effects" used herein means dyschromatosis judged by 70% or more panelists to be "dyschromatosis having no alleviation" when tested by a method described in Example 2 or the like using a tyrosinase inhibitor (e.g., arbutin).

The skin preparation for external use of the present invention can be produced by treating the above-described essential ingredient and an optional ingredient according to a standard method.

EXAMPLES

Although the present invention will more fully be described hereinafter with reference to Examples, it is understood that the present invention is not intended to be limited only to such Examples.

Example 1

According to a method shown below, inhibitory action on the elongation of dendrites was examined using human melanocytes. (Reagent, etc.) Cells, basal media, and amplification additives were purchased from KURABO INDUSTRIES LTD.

(Cell) Normal human melanocyte (Medium) Basal medium (Medium 154S) supplemented with reagents described below (Reagent) Amplification additive: bovine pituitary extract (BPE) (final concentration of 0.4% v/v in the medium), fetal bovine serum (FBS) (final concentration of 0.5% v/v in the medium), human recombinant basic fibroblast growth factor (rFGF-B) (final concentration of 3 ng/ml in the medium), hydrocortisone (final concentration of 0.18 µg/ml in the medium), insulin (final concentration 5 µg/ml in the medium), transferrin (final concentration of 5 µg/ml in the medium), phorbol 12-myristate 13-acetate (PMA) (final concentration of 10 ng/ml in the medium), heparin (final concentration of 3 µg/ml in the medium), and PSA solution (mixture solution of penicillin concentration of 50,000 Unit/ml, streptomycin concentration of 50 µg/ml, and amphotericin B concentration of 12.5 µg/ml; 1-ml addition with respect to 500 ml of the medium)

(Method)

Compound 1 (methylophiopogonanone B) obtained in the above-described example of production was diluted in a basal medium so that the concentration was brought up to 100 µg/ml, to make a sample solution. It is noted that a control is a solution having only a basal medium.

Normal human melanocytes were inoculated into a 48-well microplate (3,000 cells/well, 200 µl medium) and cultured at 37° C.

After 24 hours, 50 µl of the sample solution was added thereto.

After 24 hours of the addition of the sample solution, inhibition against the elongation of dendrites was observed.

(Result)

The result is shown in Table 1 by the length of the dendrite. It is seen that the dendrite is elongated in the control by the effect of adding the growth factor, while elongation is inhibited in the added group of Compound 1.

TABLE 1

| Added compound | Length of dendrite (μm) |
|---|---|
| Compound 1 | 22 ± 6 |
| Control | 140 ± 29 |

Example 2

According to a prescription shown below, a cosmetic that was a skin preparation for external use of the present invention was prepared. That is, ingredients of I, II, and III each were heated to 70° C. II was neutralized with III and emulsified by gradually adding I with stirring. There resulting mixture was homogenized with a homogenizer, followed by cooling with stirring to give a milky lotion. Comparative Example 1 in which Compound 1 in this prescription was substituted by squalene was made. Twenty persons in total (10 persons for 1 group) suffering from dark complexion that was not alleviated by usual cosmetics for inhibiting the production of melanin were used to examine the degree of alleviation of dark complexion in a usage test with use at twice in the morning and evening for 30 consecutive days. The degree of alleviation was evaluated after 30-day use by scores of Score 5: significantly alleviated, Score 4: obviously alleviated, Score 3: alleviated, Score 2: slightly alleviated, and Score 1: not alleviated. The result is shown in Table 2. This reveals that the cosmetic that is the skin preparation for external use of the present invention has excellent whitening effect.

I

| Squalene | 10 parts by weight |
|---|---|
| Sorbitan sesquistearate | 2 parts by weight |
| Compound 1 | 0.005 part by weight |
| Butylparaben | 0.1 part by weight |

II

| 1,3-buthanediol | 5 parts by weight |
|---|---|
| Xanthan gum | 0.1 part by weight |
| Acrylate alkyl-methacrylate alkyl (C10–30) | 0.4 part by weight |
| Methylparaben | 0.1 part by weight |
| Water | 50 parts by weight |

III

| Potassium hydroxide | 0.2 part by weight |
|---|---|
| Water | 32.095 parts by weight |

TABLE 2

| Sample | Score 5 | Score 4 | Score 3 | Score 2 | Score 1 |
|---|---|---|---|---|---|
| Example 2 | 1 | 1 | 6 | 2 | |
| Comparative Example 1 | | | | 2 | 8 |

Example 3

A skin preparation for external use (cosmetic) was made in the same way as in Example 2 except that the amount of Compound 1 was changed, and similarly evaluated using 10 similar panelists. Similar effect was observed in this skin preparation for external use.

I

| Squalene | 10 parts by weight |
|---|---|
| Sorbitan sesquistearate | 2 parts by weight |
| Compound 1 | 0.01 part by weight |
| Butylparaben | 0.1 part by weight |

II

| 1,3-buthanediol | 5 parts by weight |
|---|---|
| Xanthan gum | 0.1 part by weight |
| Arylate alkyl-methacrylate alkyl (C10–30) | 0.4 part by weight |
| Methylparaben | 0.1 part by weight |
| Water | 50 parts by weight |

III

| Potassium hydroxide | 0.2 part by weight |
|---|---|
| Water | 32.09 parts by weight |

TABLE 3

| Sample | Score 5 | Score 4 | Score 3 | Score 2 | Score 1 |
|---|---|---|---|---|---|
| Example 3 | 1 | 4 | 3 | 2 | |

Example 4

According to a prescription shown below, a skin preparation for external use (cosmetic) was made in the same way as in Examples 2 and 3, and similarly evaluated using similar panelists. Comparative Example 2 in which Compound 1 was substituted by arbutin was made and similarly evaluated. The results are shown in Table 4. This reveals that less whitening effect of the tyrosinase inhibitor was observed in the panelists and that the dendrite elongation inhibitor for melanocytes of the present invention was observed to effectively act even in such panelists.

I

| Squalene | 10 parts by weight |
|---|---|
| Sorbitan sesquistearate | 2 parts by weight |
| Compound 1 | 1 part by weight |
| Butylparaben | 0.1 part by weight |

II

| 1,3-buthanediol | 5 parts by weight |
|---|---|
| Xanthan gum | 0.1 part by weight |
| Acrylate alkyl-methacrylate alkyl (C10–30) | 0.4 part by Weight |
| Methylparaben | 0.1 part by weight |
| Water | 50 parts by weight |

III

| Potassium hydroxide | 0.2 part by weight |
|---|---|
| Water | 31.1 parts by weight |

TABLE 4

| Sample | Score 5 | Score 4 | Score 3 | Score 2 | Score 1 |
|---|---|---|---|---|---|
| Example 4 | 2 | 4 | 4 | | |
| Comparative Example 2 | | | | 3 | 7 |

INDUSTRIAL APPLICABILITY

According to the present invention, a useful ingredient for inhibiting the elongation of melanocytic dendrites and alleviating, by this action, dyschromatosis on which melanin production inhibitors utilizing usual tyrosinase inhibitory action are not or less effective can be provided.

What is claimed is:

1. A method for inhibiting elongation of melanocytic dendrites comprising:

a step of applying to skin, a skin preparation for external use, for inhibiting elongation of melanocytic dendrites wherein the skin preparation comprises, as an active ingredient, a dendrite elongation inhibitor for melanocytes consisting of methylophiopogonanone B indicated by the following formula:

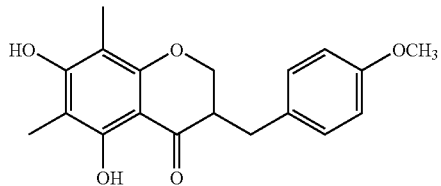

and/or a salt thereof.

2. The method for inhibiting elongation of melanocytic dendrites according to claim 1, wherein the skin preparation for external use is used for reducing dyschromatosis on which tyrosinase inhibitors have insufficient effect.

3. The method for inhibiting elongation of melanocytic dendrites according to claim 1, wherein the skin preparation for external use is a cosmetic.

4. The method for inhibiting elongation of melanocytic dendrites according to claim 2, wherein the skin preparation for external use is a cosmetic.

* * * * *

UNITED STATES PATENT AND TRADEMARK OFFICE
CERTIFICATE OF CORRECTION

PATENT NO. : 7,141,601 B2  
APPLICATION NO. : 10/536675  
DATED : November 28, 2006  
INVENTOR(S) : Tada et al.

It is certified that error appears in the above-identified patent and that said Letters Patent is hereby corrected as shown below:

Title Page, item [73] (Assignee) "Pola Chemiocal Industries Inc." should be changed to --Pola Chemical Industries Inc.--

Title Page, Column 2, Line 5, "Chemical & pharmaceuticla Bulletin" should be changed to --Chemical & Pharmaceutical Bulletin--

Page 1, Column 2, Lines 13-14, "Chemical & Pharmaceutical Buletin" should be changed to --Chemical & Pharmaceutical Bulletin--

Column 2, Line 9, "Chemical & Pharmaceutical Bulltin" should be changed to --Chemical & Pharmaceutical Bulletin--

Column 3, Line 61, "maybe the entire plant," should be changed to --may be the entire plant--

Column 3, Line 61, "apart of the plant" should be changed to --a part of the plant--

Column 4, Line 9, "such as ethyl-acetate" should be changed to --such as ethyl acetate--

Column 5, Line 36, "polyexyethylene alkyl ether" should be changed to --polyoxyethylene alkyl ether--

Column 7, Lines 20-21, "There resulting mixture" should be changed to --The resulting mixture--

UNITED STATES PATENT AND TRADEMARK OFFICE
CERTIFICATE OF CORRECTION

PATENT NO. : 7,141,601 B2
APPLICATION NO. : 10/536675
DATED : November 28, 2006
INVENTOR(S) : Tada et al.

It is certified that error appears in the above-identified patent and that said Letters Patent is hereby corrected as shown below:

Column 7, Line 48, "alkyl (C10-30)" should be changed to --to alkyl ($_{C10-30}$)--

Signed and Sealed this

Nineteenth Day of June, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,141,601 B2 |
| APPLICATION NO. | : 10/536675 |
| DATED | : November 28, 2006 |
| INVENTOR(S) | : Tada et al. |

It is certified that error appears in the above-identified patent and that said Letters Patent is hereby corrected as shown below:

Title Page, item [73] (Assignee) "Pola Chemiocal Industries Inc." should be changed to --Pola Chemical Industries Inc.--

Title Page, Column 2, Line 5, "Chemical & pharmaceuticla Bulletin" should be changed to --Chemical & Pharmaceutical Bulletin--

Page 1, Column 2, Lines 13-14, "Chemical & Pharmaceutical Buletin" should be changed to --Chemical & Pharmaceutical Bulletin--

Column 2, Line 9, "Chemical & Pharmaceutical Bulltin" should be changed to --Chemical & Pharmaceutical Bulletin--

Column 3, Line 61, "maybe the entire plant," should be changed to --may be the entire plant--

Column 3, Line 61, "apart of the plant" should be changed to --a part of the plant--

Column 4, Line 9, "such as ethyl-acetate" should be changed to --such as ethyl acetate--

Column 5, Line 36, "polyexyethylene alkyl ether" should be changed to --polyoxyethylene alkyl ether--

Column 7, Lines 20-21, "There resulting mixture" should be changed to --The resulting mixture--

UNITED STATES PATENT AND TRADEMARK OFFICE
CERTIFICATE OF CORRECTION

PATENT NO. : 7,141,601 B2
APPLICATION NO. : 10/536675
DATED : November 28, 2006
INVENTOR(S) : Tada et al.

It is certified that error appears in the above-identified patent and that said Letters Patent is hereby corrected as shown below:

Column 7, Line 48, "alkyl (C10-30)" should be changed to --alkyl ($C_{10-30}$)--

This certificate supersedes Certificate of Correction issued June 19, 2007.

Signed and Sealed this

Twenty-fifth Day of September, 2007

JON W. DUDAS
*Director of the United States Patent and Trademark Office*